US00PP24537P3

(12) United States Plant Patent
Abrahamson et al.

(10) Patent No.: US PP24,537 P3
(45) Date of Patent: Jun. 10, 2014

(54) WILLOW PLANT NAME 'PREBLE'

(50) Latin Name: *Salix viminalis×(Salix sachalinensis×Salix miyabeana)*
Varietal Denomination: Preble

(75) Inventors: Lawrence P. Abrahamson, Marcellus, NY (US); Richard F. Kopp, Marietta, NY (US); Lawrence B. Smart, Geneva, NY (US); Timothy A. Volk, Syracuse, NY (US)

(73) Assignee: Suny Research Foundation, Albany, NY (US)

( * ) Notice: Subject to any disclaimer, the term of this patent is extended or adjusted under 35 U.S.C. 154(b) by 158 days.

(21) Appl. No.: 13/385,672

(22) Filed: Feb. 29, 2012

(65) Prior Publication Data

US 2013/0227752 P1 Aug. 29, 2013

(51) Int. Cl.
*A01H 5/00* (2006.01)

(52) U.S. Cl.
USPC ..... Plt./226

(58) Field of Classification Search
USPC ..... Plt./216, 226
See application file for complete search history.

(56) References Cited

U.S. PATENT DOCUMENTS

PP17,646 P2 * 4/2007 Abrahamson et al. ..... Plt./216
PP17,682 P2 * 5/2007 Abrahamson et al. ..... Plt./216
PP17,710 P3 * 5/2007 Abrahamson et al. ..... Plt./216
PP17,724 P3 * 5/2007 Abrahamson et al. ..... Plt./216
PP17,845 P3 * 7/2007 Abrahamson et al. ..... Plt./226
PP17,946 P3 * 8/2007 Abrahamson et al. ..... Plt./216
PP17,997 P3 * 9/2007 Abrahamson et al. ..... Plt./216

OTHER PUBLICATIONS

Hangs, R.D. et al., "Examining the salt tolerance of willow (*Salix* spp.) bioenergy species for use on salt-affected agricultural lands", 2011 Can. J. Plant Sci. 91 (pp. 509-517) No. 3 May 2011.

* cited by examiner

*Primary Examiner* — Wendy C Haas
(74) *Attorney, Agent, or Firm* — Harris Beach PLLC

(57) ABSTRACT

A distinct female cultivar of *Salix viminalis×(Salix sachalinensis×Salix miyabeana)* named 'Preble', characterized by rapid stem growth producing 29% more woody biomass than the average of three current production cultivars (*Salix×dasyclados* 'SV1' (unpatented), *Salix sachalinensis* 'SX61' (unpatented), and *Salix miyabeana* 'SX64' (unpatented)) when grown in the same field for the same length of time (three growing seasons after coppice) in two different trials in Constableville, N.Y. and Middlebury, Vt. 'Preble' can be planted from dormant stem cuttings, produces multiple stems after coppice and the stem biomass can be harvested when the plant is dormant. In the spring following harvest, the plant will re-sprout very vigorously, producing new stems that can be harvested repeatedly after two to four years of growth. 'Preble' displays a low incidence of rust disease and is not damaged by potato leafhoppers.

11 Drawing Sheets

STATEMENT REGARDING FEDERALLY SPONSORED RESEARCH OR DEVELOPMENT

This invention was made with government support under contract 00-EXCA-1-0890 awarded by the U.S. Department of Agriculture/ National Institute of Food and Agriculture (NIFA), under contract no. 68-3A75-6-500 awarded by the U.S. Department of Agriculture, and under contract no. DE-AC05-00OR22725 awarded by Department of Energy. The government has certain rights in this invention.

1. LATIN NAME OF THE GENUS AND SPECIES OF THE PLANT CLAIMED

*Salix viminalis×(Salix sachalinensis* (also known as *Salix udensis*)*×Salix miyabeana*).

2. VARIETY DENOMINATION

Preble.

3. BACKGROUND OF THE INVENTION

1. Field of the Invention

The invention is a new and distinct cultivar known by the cultivar epithet 'Preble' resulting from the novel hybridization of *Salix viminalis* with a hybrid of *Salix sachalinensis×Salix miyabeana*. The new cultivar was produced through controlled willow breeding conducted by the inventors in Syracuse, N.Y. The objective of the breeding program is to produce new willow cultivars that generate high biomass yields on a variety of sites, are resistant to diseases and pests, and possess agronomic traits suitable for mechanical planting, harvesting, and post-harvest processing. Shrub willow is being developed as an agricultural plant that will be grown and harvested as a sustainable, renewable source of energy. Once a field planting of shrub willows is established, the woody stems can be harvested every two to four years, and new shoots will re-sprout the following season. Repeated harvesting every two to four years can be sustained for at least 15 years.

2. Description of Relevant Prior Art

The invention is related to the following plant patents, all of which are assigned to the Research Foundation of the State University of New York: Fast-Growing Shrub Willow Named 'Fish Creek', U.S. Plant Pat. No. 17,710; Fast-Growing Shrub Willow Named 'Canastota', U.S. Plant Pat. No. 17,724; Fast-Growing Shrub Willow Named 'Millbrook', U.S. Plant Pat. No. 17,646; Fast-Growing Shrub Willow Named 'Oneida', U.S. Plant Pat. No. 17,682; Fast-Growing Shrub Willow Named 'Otisco', U.S. Plant Pat. No. 17,997; Fast-Growing Shrub Willow Named 'Tully Champion', U.S. Plant Pat. No. 17,946; and Fast-Growing Shrub Willow Named 'Owasco', U.S. Plant Pat. No. 17,845. The cultivar of fast-growing shrub willow named 'Preble' was produced in the same willow breeding program as were the other cultivars listed above.

This new cultivar of *Salix viminalis*×(*Salix sachalinensis*×*Salix miyabeana*) was the seedling progeny of the controlled pollination of the female clone *Salix viminalis* 'SV2' (unpatented) by the male clone *Salix sachalinensis*×*Salix miyabeana* '9970-037' (unpatented) performed in February 2001 in Syracuse, N.Y. The plant has been propagated repeatedly by stem cuttings in Syracuse, N.Y. and has been found to retain its distinctive characteristics through successive generations of asexual propagation.

The parent clone *Salix viminalis* 'SV2' (unpatented) was originally transferred in 1990 from a breeding program in Toronto, Ontario, Canada to a willow breeding program in Syracuse, N.Y. and was vegetatively propagated from stem cuttings. The male parent, *Salix sachalinensis*×*Salix miyabeana* '9970-037' (unpatented), was produced through controlled breeding in 1999 and is a progeny of *Salix sachalinensis* 'SX61' (unpatented) crossed with *Salix miyabeana* 'SX64' (unpatented). The growth of the parent plants was characterized in nursery plantings in Tully, N.Y. The male clone *Salix sachalinensis*×*Salix miyabeana* '9970-037' (unpatented) displayed rapid stem growth and low incidence of rust disease, so was chosen to serve as a parent in a cross with *S. viminalis* 'SV2'(unpatented), which suffered from susceptibility to the potato leafhopper (*Empoasca fabae*). The seedlings produced by this cross (identification #01X-268) were first established in a greenhouse, and then were transplanted to a field in Syracuse, N.Y. This particular individual (identification #01X-268-015) was selected from the family due to its exceptional stem height growth.

The new cultivar has been grown in Syracuse, N.Y. and Tully, N.Y., which have a normal yearly average daily temperature of 47° F., normal daily maximum temperature in July of 82° F., normal daily minimum temperature in January of 14° F., and average precipitation of 40 inches. The new cultivar grows from a rooted cutting to a fully mature plant ready for harvest in approximately two to four years.

This cultivar was described as displaying greater salt tolerance than many other *Salix* spp. genotypes in a paper by R. D. Hangs, J. J. Schoenau, K. C. J. Van Rees, and H. Steppuhn "Examining the salt tolerance of willow (*Salix* spp.) bioenergy species for use on salt-affected agricultural lands" (2011) *Canadian Journal of Plant Science,* 91:509-517.

4. SUMMARY OF THE INVENTION

The *Salix viminalis*×(*Salix sachalinensis*×*Salix miyabeana*) cultivar 'Preble' has not been observed under all possible environmental conditions. The phenotype may vary somewhat with variations in environments such as temperature, light intensity and length of illumination, without, however, any variation in genotype. The new and distinct cultivar presents the following traits that have been repeatedly observed and are determined to be the unique characteristics of 'Preble'. These characteristics in combination distinguish 'Preble' as a new and distinct cultivar:

'Preble' has rapid growth rate, producing 29% more woody biomass than the average of three current production clones (*Salix*×*dasyclados* 'SV1' (unpatented), *Salix sachalinensis* 'SX61' (unpatented) and *Salix miyabeana* 'SX64' (unpatented)) across two sites: Constableville, N.Y. and Middlebury, Vt. At Constableville, N.Y., a site with marginal soils and a short growing season, 'Preble' produced 35% greater biomass than one of its grandparents (*Salix sachalinensis* 'SX61') (unpatented) and 71% greater biomass than another of its grandparents (*Salix miyabeana* 'SX64' (unpatented)), and 12% more biomass than another production clone (*Salix*×*dasyclados* 'SV1' (unpatented)) when grown in the same field for the same length of time (three growing seasons after coppice). In the Middlebury, Vt. trial, 'Preble' produced 18% and 27% greater biomass than its grandparents, 'SX61' (unpatented) and 'SX64' (unpatented) respectively, and 30% greater biomass than 'SV1' (unpatented) when grown in the same field for three growing seasons after coppice.

'Preble' has resistance to potato leafhopper, which causes severe stunting of growth, curling of the leaves, and overall decline in vigor (all characteristic of hopper burn) on the female parent, *S. viminalis* 'SV2' (unpatented) assessed in experimental trials conducted in Fredonia, N.Y. and Constableville, N.Y.

'Preble' has a low incidence of rust disease assessed in experimental trials in Fredonia, N.Y. and Constableville, N.Y.

'Preble' has mature leaves that are lanceolate, have an acuminate apex and a cuneate base, are typically 13-15 cm in length and 2.2-2.6 cm in width, lustrous, glabrous, frequently undulate along the edges, with serrate to crenate margins. The leaves of the female parent *S. viminalis* 'SV2' (unpatented), by contrast, are thin and linear. The leaves of the male parent '9970-037' (unpatented) are more oblong with acute apex, acute to obtuse base, typically 8.5-12.0 cm in length and 1.7-2.1 cm in width.

'Preble' has dormant vegetative buds that are lanceolate, whereas 'SV2' (unpatented) has buds that are smaller and ovate.

5. BRIEF DESCRIPTION OF THE DRAWINGS

The accompanying color photographs show the features of the claimed cultivar in a manner as true as is reasonably possible.

FIG. 1.1. The bark of a three-year-old portion of stem collected while dormant.

FIG. 1.2. One-year-old portion of stem collected while dormant.

FIG. 1.3. Vegetative bud in dormancy.

FIG. 1.4. Floral bud in dormancy, prior to abscission of the bud scale.

FIG. 1.5. Floral bud in dormancy, after abscission of the bud scale.

FIG. 1.6. New shoot growth from a stem cutting rooted in potting mix in a greenhouse.

FIG. 1.7. Upper leaf surface.

FIG. 1.8. Lower leaf surface.

FIG. 1.9. Mature catkin.

FIG. 1.10. Pistil and densely pubescent floral bract.

FIG. 2.1. Mean stem biomass yield produced by 'Preble' over three growing seasons post-coppice in four eighteen-plant plots in Constableville, N.Y. harvested in December 2009.

FIG. 2.2. Mean stem biomass yield produced by 'Preble' over three growing seasons post-coppice in four eighteen-plant plots growing in Middlebury, Vt. harvested in December 2010.

6. DETAILED BOTANICAL DESCRIPTION

The following detailed description sets forth characteristics of the new plant. The following observations and measurements describe plants grown by asexual reproduction in Geneva, N.Y. under conditions as described hereinabove. Color references are made using The Royal Horticultural Society Colour Chart, Fourth Edition, 2001 (hereinafter The R.H.S. Colour Chart) of The Royal Horticultural Society of London, England, except where general terms of ordinary dictionary significance are used.

The following detailed description of the 'Preble' variety is based on observations from 10 inch cuttings grown in a greenhouse in Geneva, N.Y. Cuttings were grown in 'Cornell mix' potting mix under natural light from December 2011 to February 2012. Plants were irrigated with automatic drip irrigation for 5 minutes each day.

Parentage:

*Female or seed parent.*—*S. viminalis* 'SV2' (unpatented).

*Male or pollen parent: Salix sachalinensis*×*Salix miyabeana* '9970-037' (unpatented).

Propagation:

*Type*.—Stem cutting.

*Time to rooting*.—Approximately 7 days in well-watered potting mix at 22° C.

Precocity: Precocious — Catkins mature several days before leaves break bud.

Plant description: One-year-old stems are on average 1.1 cm in diameter at a height of 1 m and an average plant produces 22 stems in the first year after coppice. The color of one-year-old stems observed during the winter when dormant are lustrous and yellow-green (RHS 153B) with portions of greyed-orange (RHS N167A). Dormant vegetative buds are greyed-orange (RHS 168A) and lanceolate. Lenticels are slightly raised with red-pink centers rimmed by white. The leaves are simple and alternate with pinnate venation. Petioles are typically 6 mm in length and 1.50-1.60 mm in diameter and are light green (RHS 143C). Stipules are rare, but when present are typically 3-4 mm in length, narrow, and lanceolate. Immature leaves are pubescent on the lower side and exhibit curling of the edges. Mature leaves are lanceolate, acuminate apex, cuneate base, typically 13-15 cm in length, 2.2-2.6 cm in width, lustrous, glabrous, frequently undulate along the edges, with serrate to crenate margins. The upper surface is green (RHS 143A and RHS141B), with the lower surface only slightly lighter and more olive in hue (RHS 139C) than the upper surface after 9 weeks of growth in a greenhouse. The average plant height of a mature plant after three seasons of growth is 5-6 m with average spread at the crown of 1.0-1.5 m when grown in commercial planting spacing of 0.6×0.7 m.

Flowering description: Dormant floral buds are elongated with a caudate apex, typically 8 mm in length, slightly raised to form a very small acute angle with the stem, and greyed-red (RHS 180B) when intact. During the winter dormancy period, some floral bud scales abscise and turn greyed-purple (RHS N186C). Peduncle of catkin is 2-3 mm in length and bears four leafy bracts. Catkins are erect, typically 3 cm in length, narrowly cylindrical, 7-8 mm in diameter at the base, but narrowing at the tip, and are densely flowered. Flowers have a densely pubescent sessile ovary with a medium length style and two erect, slightly separated stigmas. Floral bract is densely pubescent with a dark obtuse apex and a mostly pink base.

Field growth characteristics: Determined through surveys of plants growing in the field in Syracuse, Tully, Geneva, and Fredonia, N.Y.

Disease resistance: Displays a low incidence of rust disease assessed in experimental trials in Fredonia, N.Y. and Constableville, N.Y.

Insect resistance: Resistance to potato leafhopper, which causes severe stunting of growth, curling of the leaves, and overall decline in vigor (all characteristic of hopper burn) on the female parent, *S. viminalis* 'SV2' (unpatented) assessed in experimental trials conducted in Fredonia, N.Y. and Constableville, N.Y.

Temperature tolerance: Stems typically do not suffer frost damage at temperatures as low as 10° F. and may suffer only minor tip dieback at lower temperatures.

Seed production: 'Preble' produces only female flowers, so viable seeds will only be produced after pollination by a compatible male variety. This has not yet been observed in field trials.

Stem features: Bark of major three-year-old stems (typically ca. 3 cm in diameter at 1 m above the ground) is greyed-green (RHS 191A) with lighter vertical streaks. Lenticels are raised, 1-3 mm across, and greyed-purple (RHS 184A). Except for the lenticels, the bark is smooth and lustrous.

Biomass yield: Mean stem biomass yield produced by 'Preble' over three growing seasons post-coppice in four eighteen-plant plots in Constableville, N.Y. harvested in December 2009 was 10.10 oven dry Mg $ha^{-1}$ $yr^{-1}$ (FIG. 2.1) and in four 18-plant plots growing in Middlebury, Vt. harvested in December 2010 was 14.15 oven dry Mg $ha^{-1}$ $yr^{-1}$ (FIG. 2.2). 'Preble' produced 29% more woody biomass than the average of three current production cultivars (*Salix*×*dasyclados* 'SV1' (unpatented), *Salix sachalinensis* 'SX61' (unpatented) and *Salix miyabeana* 'SX64' (unpatented)) across those two sites—Constableville, N.Y. and Middlebury, Vt. At Constableville, N.Y.—a site with marginal soils and a short growing season—'Preble' produced 35% greater biomass than one of its grandparents (*Salix sachalinensis* 'SX61' (unpatented)) and 71% greater biomass than another of its grandparents (*Salix miyabeana* 'SX64' (unpatented)), and 12% more biomass than another production cultivar (*Salix*×*dasyclados* 'SV1' (unpatented)) when grown in the same field for the same length of time (three growing seasons after coppice). In the Middlebury, Vt. trial, 'Preble' produced 18% and 27% greater biomass than its grandparents, 'SX61' (unpatented) and 'SX64' (unpatented) respectively, and 30% greater biomass than 'SV1' (unpatented) when grown in the same field for three growing seasons after coppice.

What is claimed is:

1. A new and distinct variety of *Salix viminalis*×(*Salix sachalinensis*×*Salix miyabeana*) shrub willow plant named 'Preble' as described and illustrated herein.

* * * * *

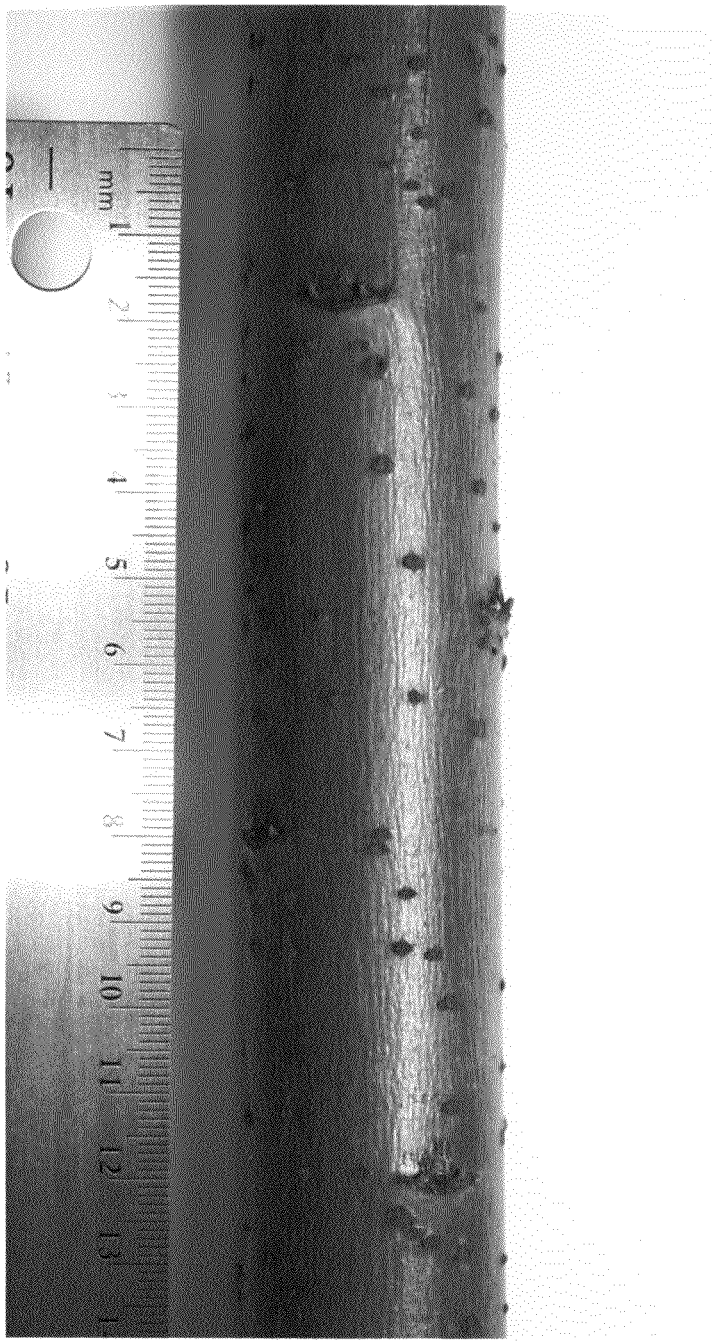
FIG. 1.1

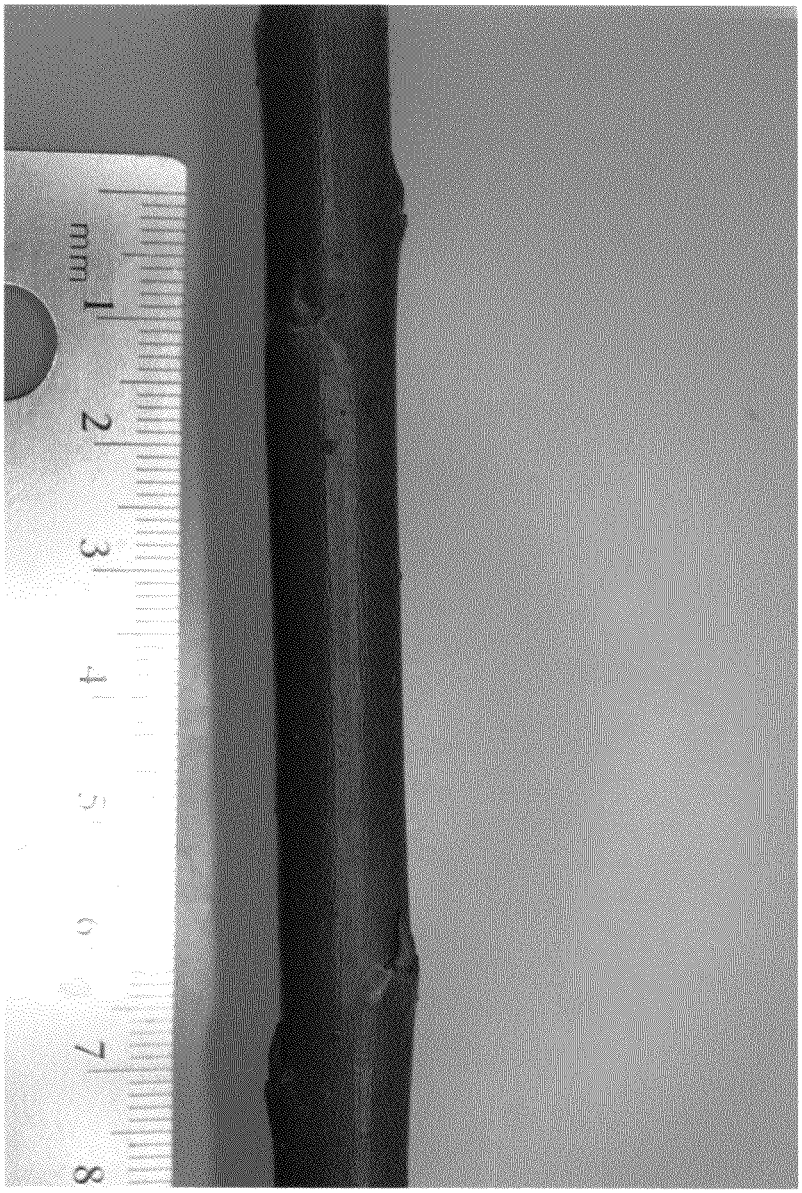
FIG. 1.2

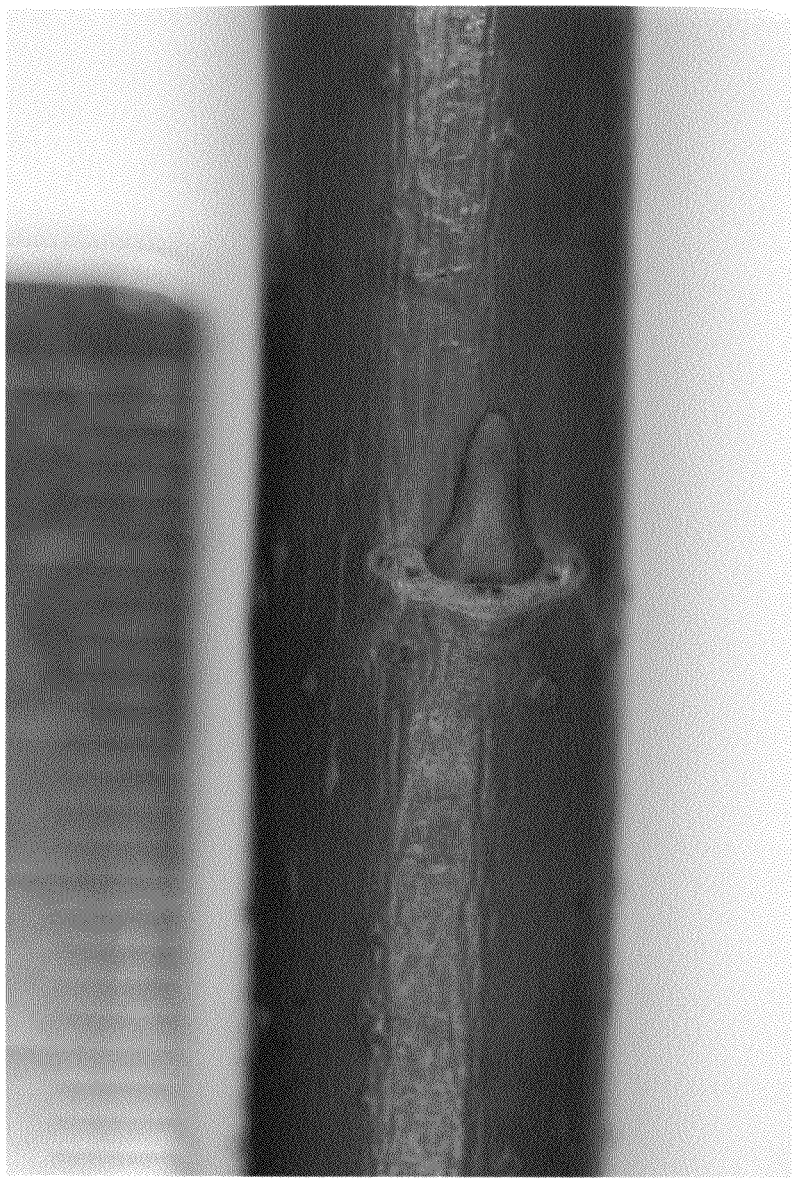
FIG. 1.3

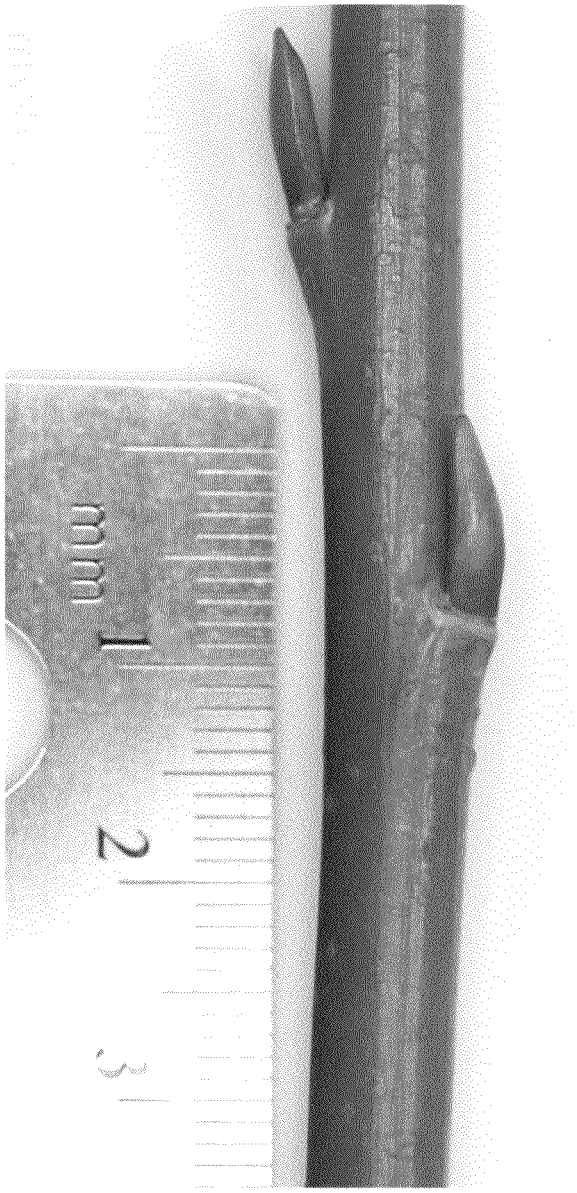
FIG. 1.4

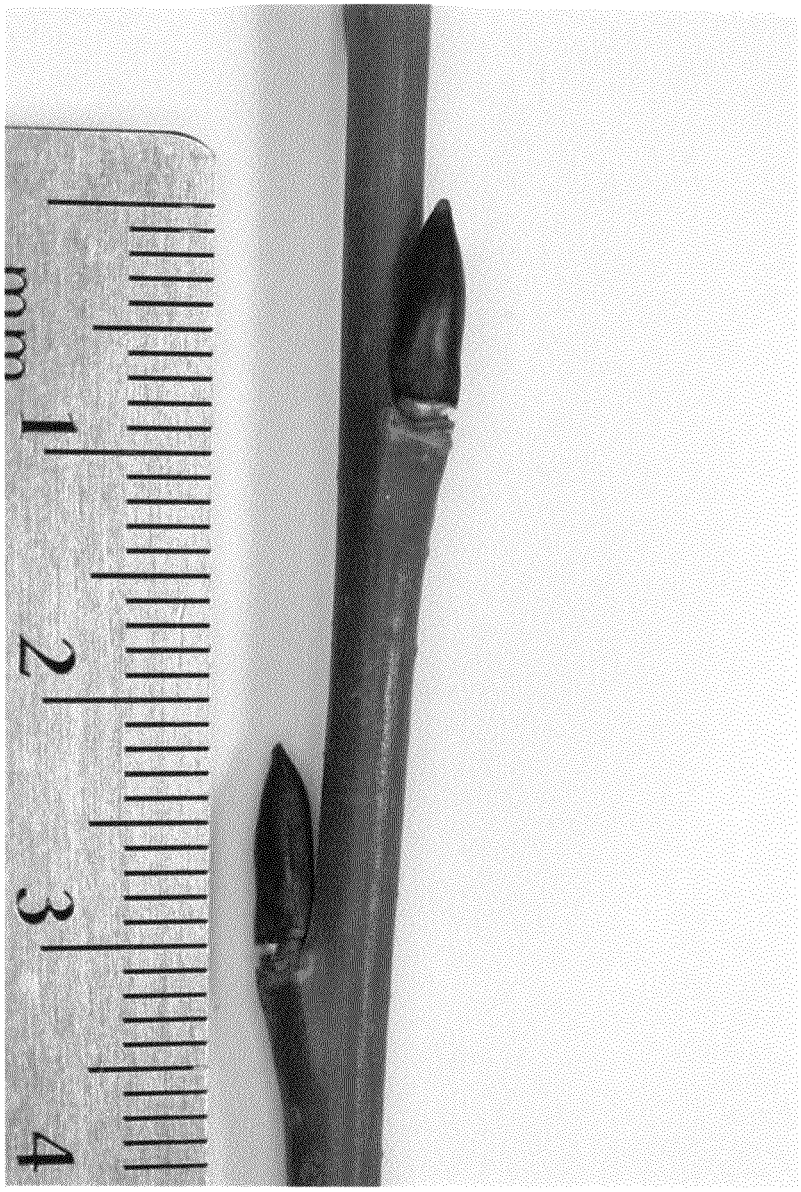
FIG. 1.5

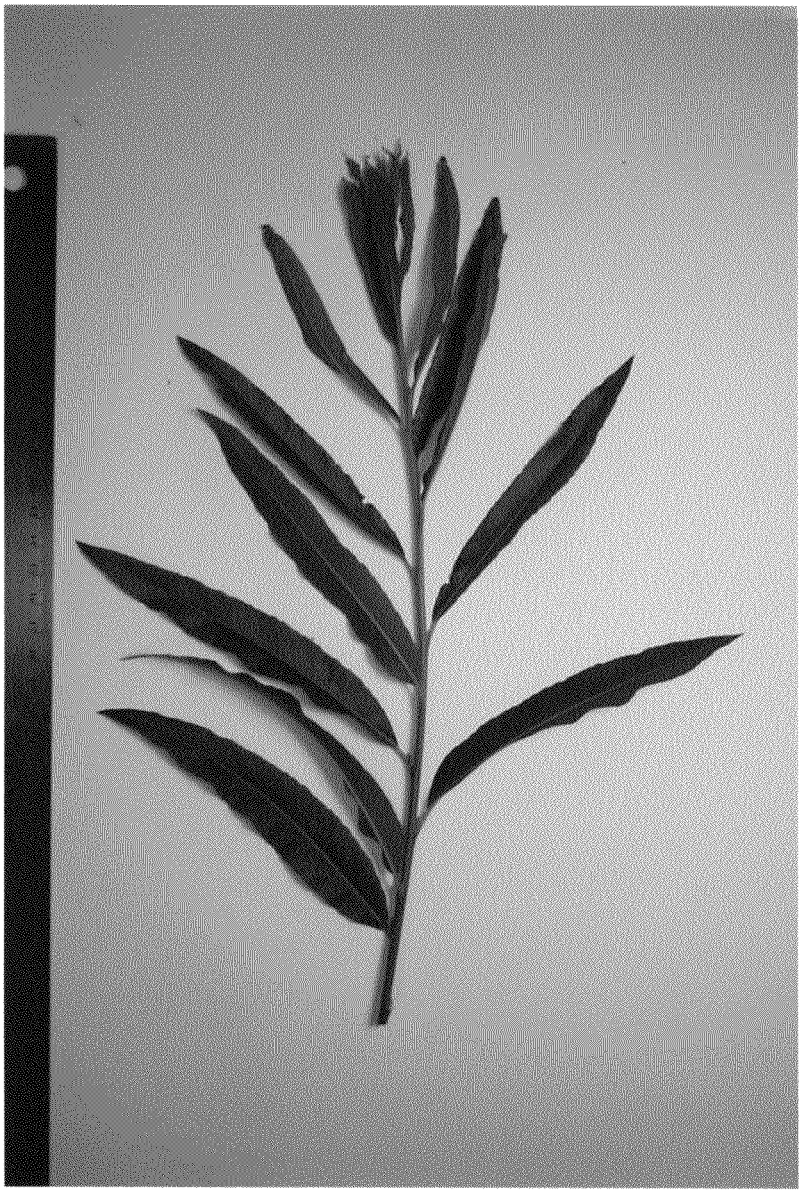
FIG. 1.6

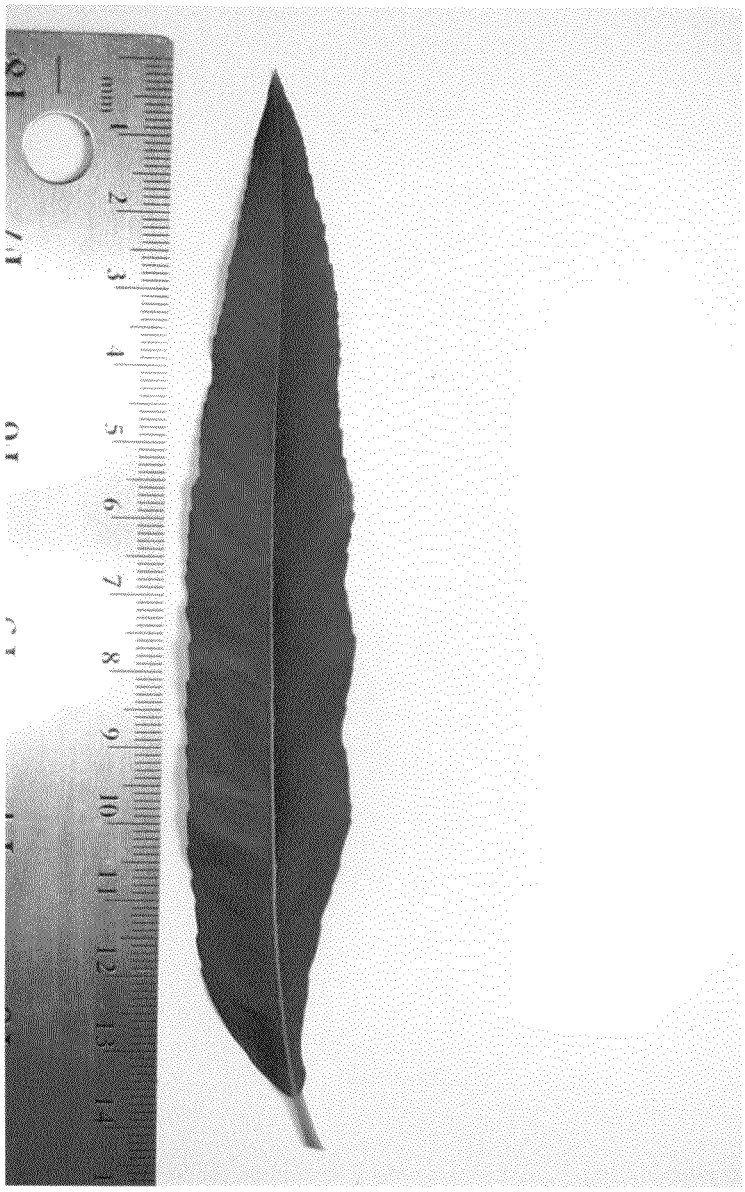
FIG. 1.7

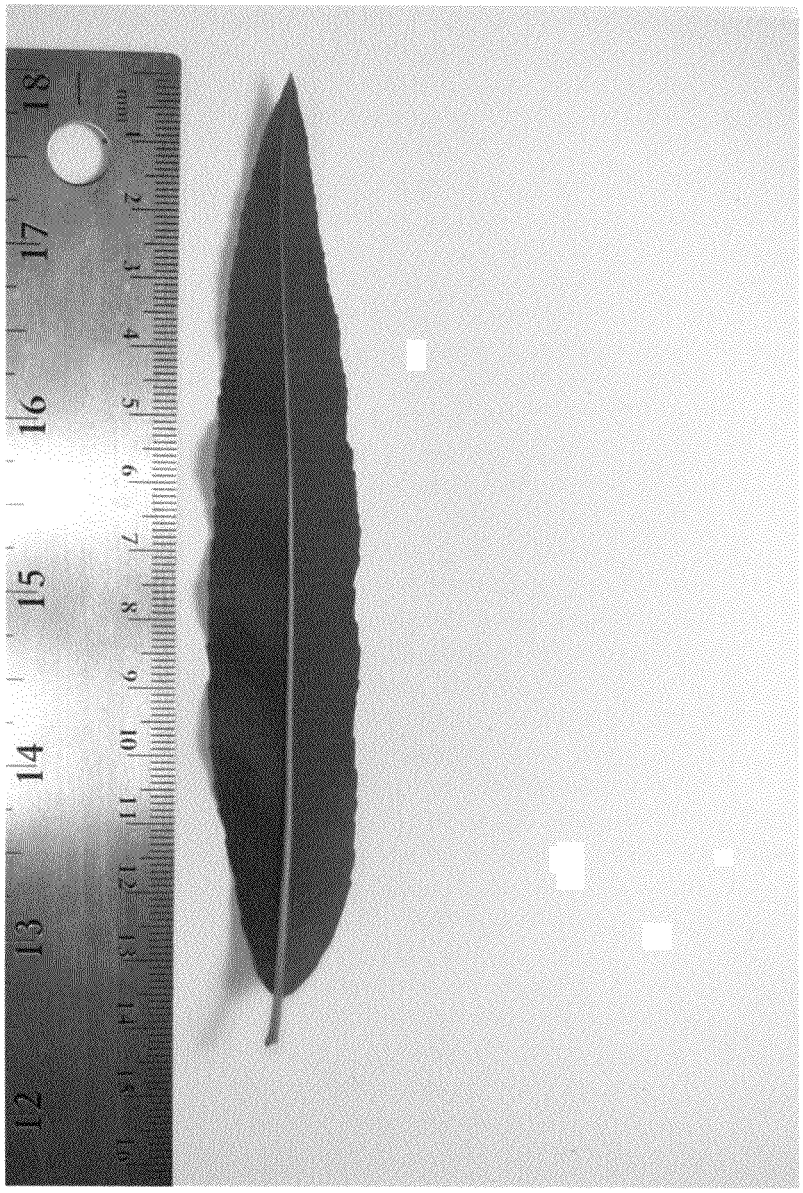
FIG. 1.8

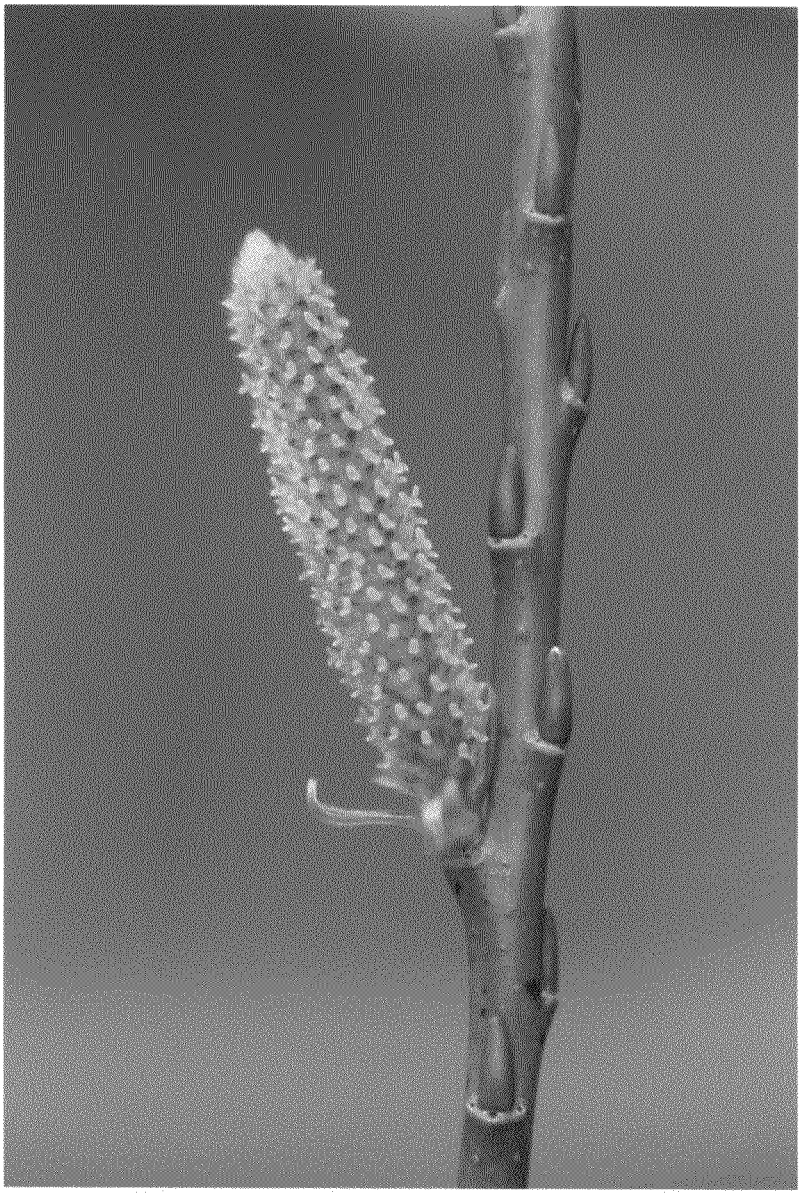
FIG. 1.9

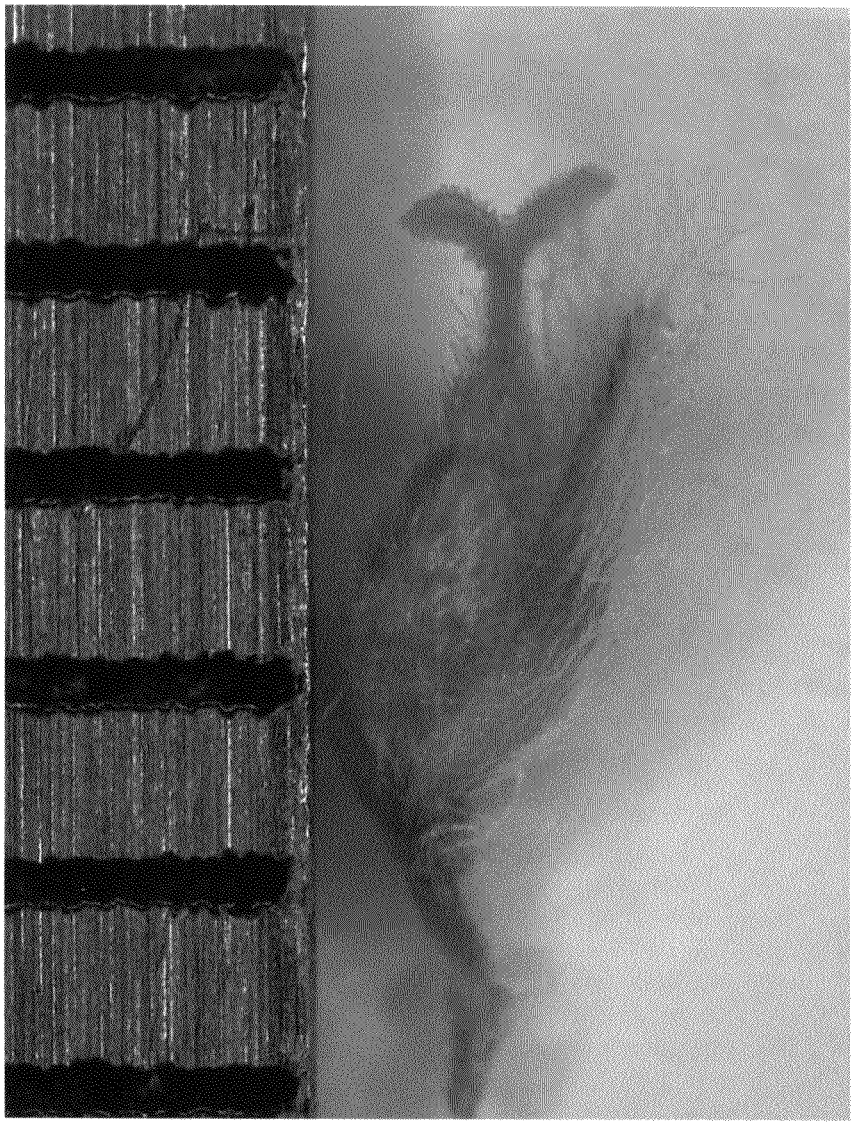
FIG. 1.10

Fig 2.1 Third-Year Harvest Yield: Constableville, NY
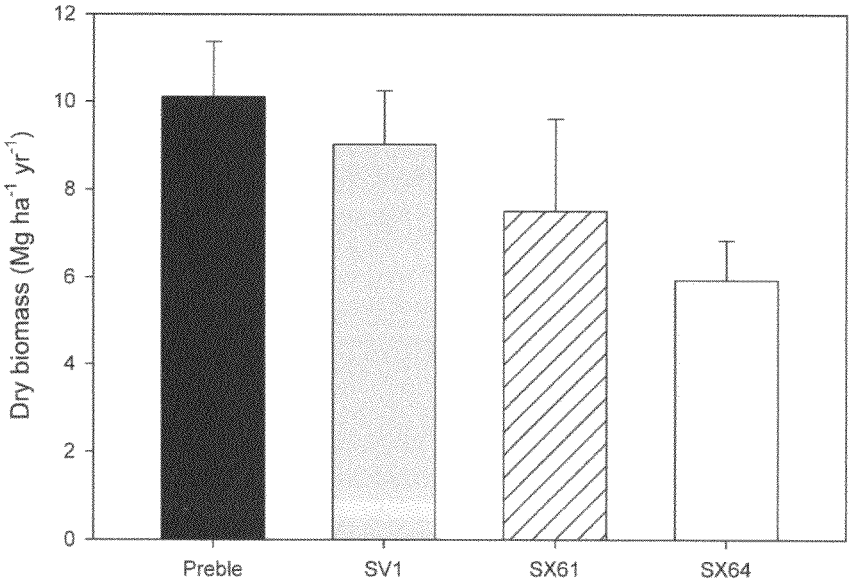
Fig 2.2 Third-Year Harvest Yield: Middlebury, VT
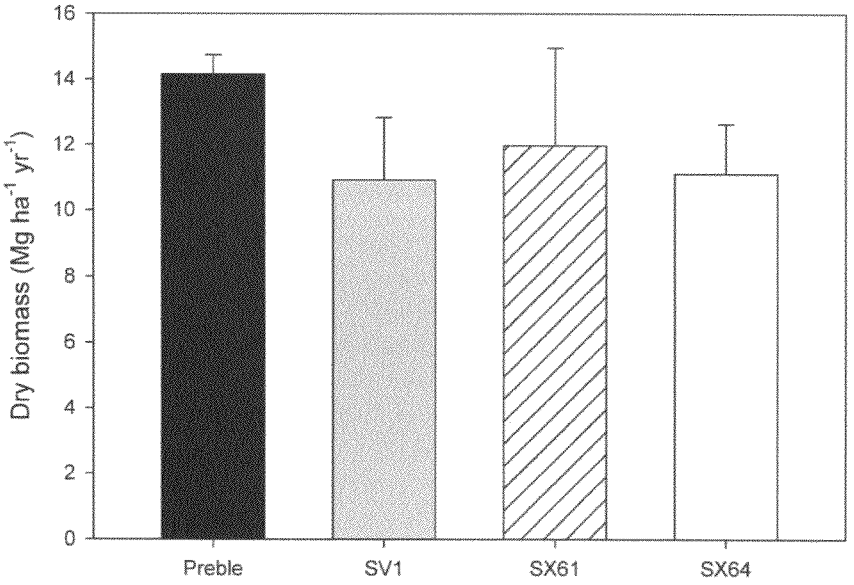
FIGS. 2.1 – 2.2